United States Patent [19]

Thyzel

[11] Patent Number: 4,911,160

[45] Date of Patent: Mar. 27, 1990

[54] APPARATUS FOR LASER SURGERY ON A PATIENT LYING ON AN OPERATING TABLE

[75] Inventor: Reinhardt Thyzel, Heroldsberg, Fed. Rep. of Germany

[73] Assignee: Meditec Reinhardt Thyzel GmbH, Heroldsberg, Fed. Rep. of Germany

[21] Appl. No.: 44,145

[22] Filed: Apr. 30, 1987

[30] Foreign Application Priority Data

Apr. 30, 1986 [DE] Fed. Rep. of Germany ....... 8611912

[51] Int. Cl.$^4$ .............................................. A61N 5/06
[52] U.S. Cl. ......................................... 606/4; 128/395
[58] Field of Search .............. 128/303.1, 362, 395–398

[56] References Cited

U.S. PATENT DOCUMENTS

| | | | |
|---|---|---|---|
| 3,528,424 | 9/1970 | Ayres | 128/303.1 |
| 3,566,872 | 3/1971 | Draeger et al. | 128/303.1 |
| 3,642,007 | 2/1972 | Roberts et al. | 128/303.1 |
| 3,720,213 | 3/1973 | Hobart et al. | 128/303.1 |
| 3,822,706 | 7/1974 | Simone et al. | 128/386 |
| 4,091,814 | 5/1978 | Togo | 128/303.1 |
| 4,144,888 | 3/1979 | Malyshev et al. | 128/303.1 |
| 4,270,845 | 6/1981 | Takizawa et al. | 128/303.1 |
| 4,309,998 | 1/1982 | Aron nee Rosa et al. | 128/303.1 |
| 4,316,474 | 2/1982 | Spethman | 128/804 |
| 4,497,319 | 2/1985 | Sekine et al. | 128/303.1 |
| 4,503,854 | 3/1985 | Jako | 128/395 |
| 4,520,816 | 6/1985 | Schachar et al. | |

FOREIGN PATENT DOCUMENTS

| | | |
|---|---|---|
| 0007256 | 1/1980 | European Pat. Off. . |
| 0145892 | 10/1984 | European Pat. Off. . |
| 2197614 | 3/1974 | France . |
| 2347025 | 11/1977 | France .............. 128/303.1 |

Primary Examiner—Lee S. Cohen
Assistant Examiner—David Shay
Attorney, Agent, or Firm—Barnes & Thornburg

[57] ABSTRACT

An apparatus for laser surgery on a patient disposed on an operating table is provided. A laser device which produces a laser beam is disposed under the operating table. A beam guiding device is also provided which guides the laser beam from the laser device laterally toward an outside side of the table, and upwardly near an outside side of the table to a point above the table. A horizontal pivot arm is also provided which receives the laser beam from the beam guiding device above the table and guides the laser beam to an operation site. The horizontal pivot arm includes an adjustable length.

14 Claims, 1 Drawing Sheet

APPARATUS FOR LASER SURGERY ON A PATIENT LYING ON AN OPERATING TABLE

BACKGROUND AND SUMMARY OF THE INVENTION

The present invention relates to an apparatus for laser surgery on a patent lying on an operating table, and in particular to an apparatus for the treatment of eyes with lasers.

Most known apparatuses for treating eyes with lasers are constructed in such a manner that the person to be treated is seated. Although the head of the person to be treated is held by a head support, and in particular a chin support during the treatment, it is unavoidable that the person to be treated shows signs of fatigue during long treatment, as required, by way of illustration, in radial keratotomy.

For that reason it is suggested that the person to be treated be laid on a bed or an operating table during treatment in order that the patient is treated in a prone position and, therefore, in a much more relaxed state.

In a known apparatus for laser eye surgery, the laser is situated beside the bed or operating table. The laser beam is guided by a "boom" to the site to be treated, and in particular the eye. The observation device is attached to the boom. By way of illustration, this observation device can be an operation microscope for example.

The known apparatuses for laser eye surgery have a number of disadvantages. The laser, typically measuring 1.5 m×0.5 m×1 m, is situated at a short distance from the operating table in such a manner that the surgeon's freedom of movement is restricted. Furthermore, the attachment of the operation microscope to the boom does not permit the freedom of movement desired in specific cases of application. Also, the manner of directing the light by means of a boom does not allow the desired freedom to adjust the operation laser beam.

An object of the present invention is to provide an apparatus for laser surgery on a patient lying on an operating table, and in particular for laser treatment of the eye, whereby the laser beam is guided to the site to be treated without encumbering the surgeon, and which permits the necessary adjustment.

These objects are achieved in accordance with the present invention by providing an apparatus for laser surgery which includes a laser device situated under an operating table. Further, a beam guiding device is positioned in proximity to the side of the table for guiding the beam from the laser device to an operating site.

In this manner, the laser device which may be in the order of 1.5×0.1×1 m as discussed above, does not restrict the freedom of movement or the available space in the treatment room.

In advantageous features of certain preferred embodiments of the invention, the beam guiding device includes a vertical guiding element in proximity to the side of the operating table. In certain preferred embodiments of the invention, the vertical guiding element is attached to a longitudinal side of the operating table.

In other advantageous features of certain preferred embodiments of the invention, particularly for laser treatment of the eye, the vertical guiding element is attached to the longitudinal side of the table in the area of a patient's chest. In all of these embodiments, the freedom movement of the surgeon and eventual assistants is practically not restricted.

In certain preferred embodiments, the use of a pivot arm, from the end of which the laser emerges and whose length is adjustable, allows any possible adjustment of the point of impact of the laser beam.

In other advantageous features of certain preferred embodiments of the invention, so-called micromanipulators or lighting devices of any design can be fitted in the pivot arm for precisely adjusting the point of impact of the laser beam, for example by tilting a mirror.

Of course, the table may be designed in a customary manner, for example being adjustable in height and/or tiltable. In any case, however, in other advantageous features of certain preferred embodiments of the invention, the pivot arm, out of which the laser emerges, is adjustable in height in such a manner that the distance between the point of emergence of the laser and its point of impact can be adjusted easily.

The invented manner of guiding the beam easily permits the fitting of a slit lamp in the apparatus in certain preferred embodiments of the invention, by way of illustration for eye operations. By way of illustration, the slit lamp can be fitted in the pivot arm, and the laser beam can be led through the slit lamp. Of course, it is also possible to provide a slit lamp which can be swivelled about an additional or the same axis as the pivot arm. Examples of slit lamps which could be used are shown in the following commonly assigned German priority applications, all filed in Germany on June 29, 1985, which are hereby incorporated by reference: P 35 23 341.9 (filed in U.S. as designated office for PCT Application No. PCT/DE 86/00268 on Mar. 2, 1987); P 35 23 342.7 (filed in U.S. as designated office for PCT Application No. PCT/DE 86/00265 on Mar. 2, 1987); and P 35 23 340.0 (filed in U.S. as designated office for PCT Application No. PCT/DE 86/00267 on Mar. 2, 1987).

In other advantageous features of certain preferred embodiments of the invention, an observing device is provided for observing surgery. In certain preferred embodiments, it is advantageous when the observation device is attached to an additional pivot arm (an observation pivot arm). By this observation pivot arm, an independent degree of freedom is permitted in adjusting the observing device in such a manner that, by way of illustration, the surgical operation can be observed from a given specific angle to the emitted laser.

In certain other preferred embodiments of the invention, the observation pivot arm, to which the observation device is fitted, further increases the possible adjustments of the observation device. For example, the observation pivot arm can be pivotable about a longitudinal axis of a vertical column which supports the observation pivot arm. The observation pivot arm can be further adjusted in height along the vertical column.

In other advantageous features of certain preferred embodiments of the invention, the observation pivot arm is provided with a plurality of bent portions. These bent portions can include additional pivot joints.

In other advantageous features of certain preferred embodiments of the invention, the observing device includes an operation microscope.

In other advantageous features of certain preferred embodiments of the invention, an operating table is included in the apparatus. The operating table includes longitudinal sides parallel to a patient lying on the table.

The longitudinal sides are bevelled around the area of the patient's head.

Other objects, advantages and novel features of the present invention will become apparent from the following detailed description of the invention when considered in conjunction with the accompanying drawings.

DETAILED DESCRIPTION OF THE DRAWINGS

Figure 1:
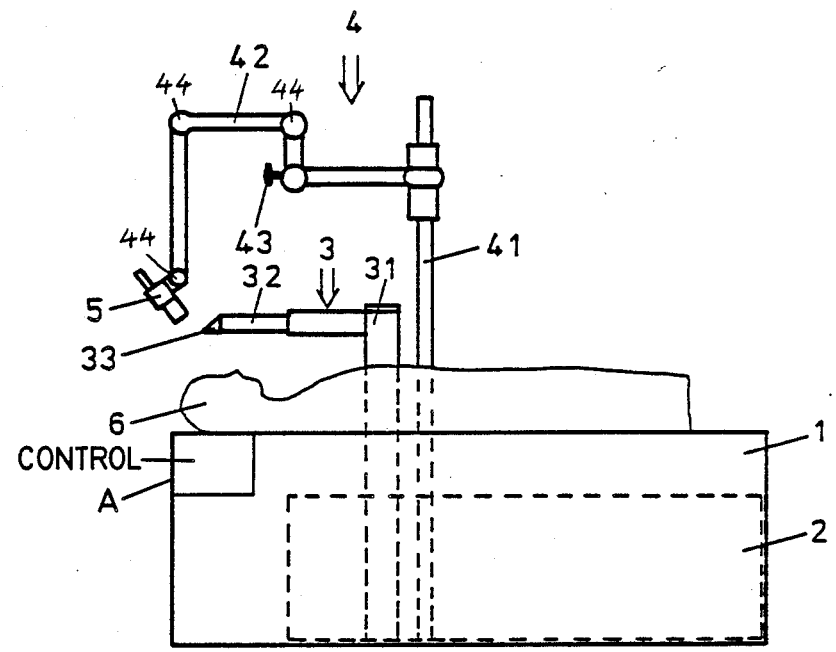
FIG. 1 is a side view of a preferred embodiment of the invention.
Figure 2:
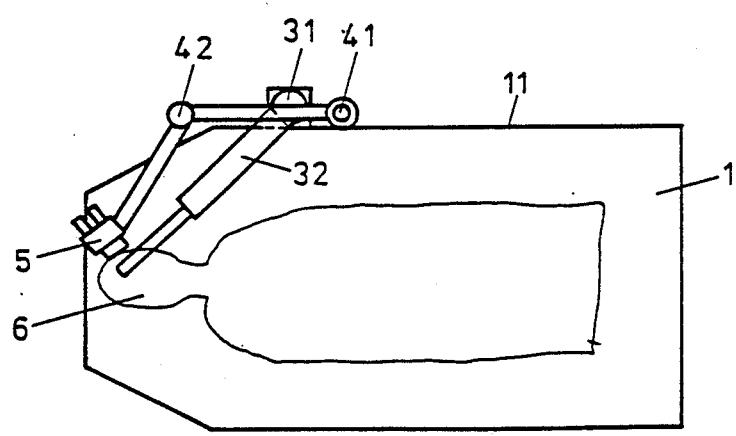
FIG. 2 is a top view of the apparatus of FIG. 1.

The preferred embodiment illustrated in FIGS. 1 and 2 is provided with a laser 2 situated under an operating table 1. In this connection, laser refers to the laser pipes including all the necessary components required for operation, such as high-voltage supply electronic control device A, etc. The operation elements of the laser as, for example, the preselection elements for output, emission time, etc., may, of course, be provided at a different site. By way of illustration, these elements can be included in the area or in one of the arrangements described below.

A beam guiding device 3 is provided, which directs the laser beam of laser 2 to the site of treatment, by way of illustration the eye of a patient 6 lying on the operating table 1. The beam guiding device 3 includes a vertical column 31, which is positioned immediately next to a longitudinal side 11 of a table. The beam guiding device further includes a pivot arm 32, adjustable in length by means of a "telescopic extension" and capable of turning about a pivot axis running through column 31. Pivot arm 32 bears a prism 33 on its tip. Further, a holder device 4 is provided for an operation microscope 5. The holder device 4 includes a vertical column 41, which is also positioned immediately next to the longitudinal side of the bed 11. A pivot arm 42 is provided which can turn about an axis of rotation running through column 41 and which can also turn about a horizontal axis of rotation by a turning screw 43. Other additional bent portions 44 can also be provided which can include additional pivot joints.

The operation of a preferred embodiment of the invention is described below. The laser beam of laser 2 first runs horizontally under operating table 1 to the longitudinal side 11 of the table. When the laser beam enters vertical column 31 it is turned upwardly 90° and led within the column to horizontal pivot arm 32. By means of an inflecting device, not depicted in detail herein, the laser beam is turned into pivot arm 32 and emerges from the pivot arm 32 after being further inflected by a prism 33 in the direction of the operating site, for example the eye of a patient 6. In certain preferred embodiments of the invention, the inflecting device can be a prism or a mirror.

Due to the swiveling capacity of the pivot arm 32 and the additional ability to adjust its length, the laser beam can be directed precisely to the desired site. Moreover, it is also possible, by way of illustration, to minutely tilt a mirror fitted to the beam guiding device 3, or to minutely tilt one of the prisms by means of a so-called micro-manipulator device in order to execute precise adjustment movements of the laser beam.

The operation microscope 5 attached to the holder device 4 serves to control the laser treatment. The microscope 5 can not only be turned about a vertical axis of rotation running through column 41, but can also be adjusted in height by moving the additional pivot arm 42 along column 41. Furthermore, after loosening turning screw 43, a part of the pivot arm 42 can be turned about an essentially horizontal axis and also swivelled about an additional vertical (and other) axes in such a manner that the operation microscope can be brought to practically any position. To help provide this adjustability of the operation microscope position, the pivot arm 42 can further include bent portions 44 which can also include pivot joints to provide additional swivel axes.

The invented apparatus has the advantage that the beam guiding device and suspension device for the operation microscope positioned in the proximity of longitudinal side 11 practically do not encumber the freedom of movement of the surgeon and any additional assistants. In this connection, in certain preferred embodiments, by way of illustration in eye operations, vertical columns 31 and 41 are set at a point around the patient's chest, and the longitudinal sides of operating table 1 are bevelled around the area of the patient's head in such a manner that the surgeon has as close as possible access to the head of the patient.

The present invention is described in the preceding in connection with a preferred embodiment by way of illustration only, without any intention to limit the scope of the general inventive idea. The most diverse modifications are possible within the general inventive idea. Of course, the inventive idea is not restricted to a specific type of a laser, but can be performed with any laser, by way of illustration argon lasers for treating the rear of the eye, neodym-YAG lasers for treating the front part of the eye, or lasers for radial keratotomy.

Furthermore, it is always also possible to utilize the inventive idea in apparatuses not intended for laser treatment of the eye, but for treatment of other parts of the body. In this case, it may, however, be advantageous to place the vertical columns, in which the laser beam is led, in other positions along the longitudinal side or to design the columns in such a manner that the columns can be moved in the direction of the longitudinal axis of the table.

Moreover, it is possible to construct the pivot arm to guide the laser beam and the observation pivot arm for the operation microscope in such manner that they can turn about the same axis of rotation.

From the preceding description of the preferred embodiments, it is evident that the objects of the invention are attained, and although the invention has been described and illustrated in detail, it is to be clearly understood that the same is by way of illustration and example only and is not to be taken by way of limitation. The spirit and scope of the invention are to be limited only by the terms of the appended claims.

What is claimed is:

1. Apparatus for laser surgery on a patient disposed on an operating table comprising:
   an operating table,
   laser means for producing a laser beam disposed under the operating table;
   beam guiding means for guiding the laser beam from the laser means laterally toward an outside side of the table, and upwardly near an outside side of the table to a point above the table; and
   horizontal pivot arm means for receiving the laser beam from the beam guiding means above the table and for guiding the laser beam to an operation site while permitting manipulated movement of the laser beam during surgery operation, said horizontal pivot arm means including an adjustable length whereby the laser beam is guided to a point above the operating table and directed to a desired site on the patient to be treated.

2. Apparatus as in claim 1, wherein said horizontal pivot arm means includes a beam exit end, said beam exit end including an inflecting means for guiding the laser beam to the operation site.

3. Apparatus as in claim 2, wherein said laser means includes electronic controlling means for controlling the operation of the laser means.

4. Apparatus as in claim 3, wherein said horizontal pivot arm means is adjustable in height from the table.

5. Apparatus as in claim 3, wherein said beam guiding means includes a vertical column, said vertical column being attached to a longitudinal side of the table.

6. Apparatus as in claim 5, wherein said vertical column of the beam guiding means is positioned at a side of the table in an area corresponding to a general position of a chest of a patient lying on the table receiving eye surgery.

7. Apparatus as in claim 5, further including an operating table, said operating table including longitudinal sides, said longitudinal sides being bevelled around the area of an end of the table at which the patient's head is disposed.

8. Apparatus as in claim 3, further including an observing means for observing the surgery connected to the table.

9. Apparatus as in claim 8, wherein said observing means is attached to an observation pivot arm, said observation pivot arm being supported by a vertical column connected to the table.

10. Apparatus as in claim 9, wherein said observation pivot arm is pivotable about a longitudinal axis of the vertical column.

11. Apparatus as in claim 9, wherein said observation pivot arm is adjustable in height along the vertical column.

12. Apparatus as in claim 9, wherein said observing means includes an operation microscope.

13. Apparatus as in claim 9, wherein said observation pivot arm includes at least one bent portion.

14. Apparatus as in claim 13, wherein said observation pivot arm includes a plurality of bent portions, at least one of said bent portions including an additional pivot joint.

* * * * *

UNITED STATES PATENT AND TRADEMARK OFFICE
CERTIFICATE OF CORRECTION

PATENT NO. :   4,911,160
DATED      :   March 27, 1990
INVENTOR(S):   Reinhardt Thyzel It is certified that error appears in the above-identified patent and that said Letters Patent is hereby corrected as shown below:

ON THE TITLE PAGE:

Item [73] Assignee:  should read --AESCULAP AG

Signed and Sealed this

Fourteenth Day of January, 1992

Attest:

HARRY F. MANBECK, JR.

*Attesting Officer*          *Commissioner of Patents and Trademarks*